United States Patent
Jayaraman et al.

(10) Patent No.: US 11,642,046 B2
(45) Date of Patent: May 9, 2023

(54) SYSTEM AND METHOD FOR SHOULDER PROPRIOCEPTIVE ANALYSIS

(71) Applicant: Tata Consultancy Services Limited, Mumbai (IN)

(72) Inventors: Srinivasan Jayaraman, Bangalore (IN); Murali Poduval, Mumbai (IN); Joshin Sahadevan, Bangalore (IN); Harshad Chandrakant Kulkarni, Bangalore (IN)

(73) Assignee: Tata Consultancy Services Limited, Mumbai (IN)

( * ) Notice: Subject to any disclaimer, the term of this patent is extended or adjusted under 35 U.S.C. 154(b) by 273 days.

(21) Appl. No.: 17/072,304

(22) Filed: Oct. 16, 2020

(65) Prior Publication Data

US 2021/0153781 A1    May 27, 2021

(30) Foreign Application Priority Data

Oct. 16, 2019   (IN) .............................. 201921041912

(51) Int. Cl.
*A61B 5/11* (2006.01)
*A61B 5/00* (2006.01)

(52) U.S. Cl.
CPC .......... *A61B 5/1122* (2013.01); *A61B 5/0022* (2013.01); *A61B 5/681* (2013.01); *A61B 5/7264* (2013.01); *A61B 2562/0219* (2013.01)

(58) Field of Classification Search
CPC ..... A61B 5/1122; A61B 5/0022; A61B 5/681; A61B 5/7264; A61B 2562/0219;
(Continued)

(56) References Cited

U.S. PATENT DOCUMENTS

2018/0224804 A1    8/2018 Berardinelli

FOREIGN PATENT DOCUMENTS

EP          3319561 A1     5/2018
WO    WO2017007929 A1     1/2017

OTHER PUBLICATIONS

Qi, Bozhao. Banerjee, Suman. "GonioSense: A Wearable-Based Range of Motion Sensing and Measurement System for Body Joints", Oct. 2016. (Year: 2016).*
(Continued)

*Primary Examiner* — Patrick Fernandes
*Assistant Examiner* — Joseph A Tombers
(74) *Attorney, Agent, or Firm* — Finnegan, Henderson, Farabow, Garrett & Dunner, LLP

(57) ABSTRACT

This disclosure relates generally to a system and method for shoulder proprioceptive analysis of the person. The present disclosure monitors the shoulder joint motion by quantitative measure of range of motion (ROM) and kinesthesia of shoulder using a smart watch, thereby assessing the limit of active motion and the ability to passively reposition the arm in space. The present disclosure estimates the ROM, velocity, quality of joint movement, direction of hand movement using the sensor data captured by the smart watch. Further, the present disclosure provides a performance metrics of the shoulder function by comparing the shoulder motion before and after a prosthesis procedure. The present disclosure implements a rule engine-based approach classifying the shoulder/arm movement which includes flexion, extension, abduction, and adduction, internal and external rotation.

18 Claims, 11 Drawing Sheets

(58) Field of Classification Search
CPC . A61B 2505/09; A61B 5/6824; A61B 5/1123; A61B 5/4528; A61B 5/1121
See application file for complete search history.

(56) References Cited

OTHER PUBLICATIONS

Bozhao Qi et al., "GonioSense: A Wearable-Based Range of Motion Sensing and Measurement System for Body Joints," MobiCom '16: Proceedings of the 22nd Annual International Conference on Mobile Computing and Networking, 2016 Publisher: Association for Computing Machinery Link: http://pages.cs.wisc.edu/~bozhao/posters/goniosense.pdf.

Michael Rigoni et al., "Assessment of Shoulder Range of Motion Using a Wireless Inertial Motion Capture Device—A Validation Study," Sensors, Apr. 13, 2019, Volume-issue Nos. vol. 19, Issue 8, Publisher: MDPI AG Link: https://www.mdpi.com/1424-8220/19/8/1781.

\* cited by examiner

SYSTEM AND METHOD FOR SHOULDER PROPRIOCEPTIVE ANALYSIS

PRIORITY CLAIM

This U.S. patent application claims priority under 35 U.S.C. § 119 to: India Application No. 201921041912, filed on Oct. 16, 2019. The entire contents of the aforementioned application are incorporated herein by reference.

TECHNICAL FIELD

This disclosure relates generally to field of shoulder assessment of a person, and more particularly to system and method for shoulder proprioceptive analysis of the person.

BACKGROUND

A shoulder has a ball and socket type of joint connecting an upper limb of the person to thorax. The movements of the shoulder are classified as flexion (forward movement), extension (backward), abduction (elevation) and internal and external rotations. The shoulder can be affected by many conditions that result in a painful and stiff joint which includes trauma, degenerative arthritis, inflammatory arthritis amongst others causing significant disability and restrictions in performing activities of daily living as well as work. Shoulder pain is very common as reported wherein 18-26% of adults are victims with this symptom.

It is necessary to measure the functionality of shoulder by some means. Measuring and characterizing shoulder motion is outwardly simple but incredibly complex in reality. On the other hand, shoulder injury recovery by rehab or surgical quantification is difficult and requires a lot of expenditure of time and effort. Clinically relevant outcomes in joint surgery and rehabilitation are determined by the increase in range and efficiency of motion in human joints as well as by the function achieved and the patient satisfaction indices.

Currently, in-clinic shoulder joint surgery and rehabilitation is attempted by a qualitative approach supported by quantitative measurement of joint motion using aids like goniometry and visual estimation of range. Existing outcome scoring systems which includes the DASH (Disabilities of the Arm, Shoulder and Hand), the Oxford score and the constant score have range of motion (ROM) as an important component wherein the character of motion is determined by clinical examination only. Further, some other systems have been exploited for the observational analysis of shoulder motion which includes maker-based system which includes Vicon, markerless system like Microsoft Kinect, robot-assisted system, wearable system.

With the advent of precision surgical technology, the number of interventions performed for the shoulder has exponentially increased and so have the needs for quantifying, characterizing and analyzing range of motion (ROM) as a surrogate marker for the improvement or deterioration of the shoulder becomes necessary. Further, continued measurement of the joint movements may provide an insight into function and mechanics of the joint as a whole which is clinically very valuable.

Currently, smart watches have the capability to detect and distinguish the gross motor movements such as walking, jogging, cycling, swimming, and sleeping. Existing apps extend to track the activity levels and basic exercise as part of patient progress, but joint range of motion in larger ball and socket joints like the hip and shoulder using unobtrusive sensing is still a challenge. Moreover, an automated portable wireless sensor system has also been developed to measure range of motion (ROM) in all planes of the major joints of the upper extremities (UE) (shoulder, elbow, radio-ulnar and wrist) and lower extremities (LE) (hip, knee and ankle) and their measurements highly correlated with those of goniometer with 95% of differences <20° and 10° for most movements in major joints of UE and LE, respectively.

SUMMARY

Embodiments of the present disclosure present technological improvements as solutions to one or more of the above-mentioned technical problems recognized by the inventors in conventional systems. For example, in one embodiment, a method for shoulder proprioceptive analysis is provided. The method comprises capturing a sensor data, specific to a shoulder movement in a plurality of phases, using a smart watch wherein the smart watch is configured to continuously monitor and quantify the shoulder movement; processing, via one or more hardware processors, the transmitted sensor data to extract a plurality of feature parameters specific to the shoulder movement in the plurality of phases; applying, via the one or more hardware processors, a rule-based engine algorithm on the captured sensor data to determine a shoulder motion classification, wherein applying the rule-based engine algorithm comprising: pre-processing a plurality of raw signals in the collected sensor data to obtain a filtered signal using a normalization technique; detecting a plurality of negative peaks using a gradient descent method and a plurality of positive peaks using a modified gradient descent method from the filtered signal; removing a plurality of false positive peaks from the detected plurality of positive peaks and removing a plurality of false negative peaks from the detected plurality of negative peaks using a reverse scanning technique; estimating an instantaneous angle of shoulder (Øs) with respect to thorax or neutral position from the filtered signal; detecting 90-degree cross point using the estimated instantaneous angle of shoulder; finding a corresponding motion gravity value (Z-axis) for the detected 90-degree cross point; classifying the shoulder motion as extension, if the motion gravity value (Z-axis) at 90-degree cross point is more than a first threshold value; finding a correlation between a motion yaw and a roll between zero-degree and 45-degree; classifying the shoulder motion as abduction, if the correlation between a motion yaw and a roll is greater than a second threshold value classifying the shoulder motion as flexion, if the correlation between the motion yaw and the roll is lesser than a second threshold value; and estimating, via the one or more hardware processors, a range of motion, associated with the shoulder motion classified among one of the extensions, abduction and flexion, using the extracted plurality of feature parameters; and a velocity, an arm movement and a performance score using the extracted plurality of feature parameters.

In another aspect, there is provided a system for securely conducting a digital examination. The system comprises: a memory storing instructions; one or more communication interfaces; and one or more hardware processors coupled to the memory via the one or more communication interfaces, wherein the one or more hardware processors are configured by the instructions to: capture, a sensor data, specific to a shoulder movement in a plurality of phases, using a smart watch wherein the smart watch is configured to continuously monitor and quantify the shoulder movement. The system further comprises processing, via one or more hardware processors, the transmitted sensor data to extract a plurality of feature parameters specific to the shoulder movement in the plurality of phases. Applying, via the one or more hardware processors, a rule-based engine algorithm on the captured sensor data to determine a shoulder motion classification, wherein applying the rule-based engine algorithm comprising: pre-processing a plurality of raw signals in the collected sensor data to obtain a filtered signal using a normalization technique; detecting a plurality of negative peaks using a gradient descent method and a plurality of positive peaks using a modified gradient descent method from the filtered signal; removing a plurality of false positive peaks from the detected plurality of positive peaks and removing a plurality of false negative peaks from the detected plurality of negative peaks using a reverse scanning technique; estimating an instantaneous angle of shoulder (Øs) with respect to thorax or neutral position from the filtered signal; detecting 90-degree cross point using the estimated instantaneous angle of shoulder; finding a corresponding motion gravity value (Z-axis) for the detected 90-degree cross point; classifying the shoulder motion as extension, if the motion gravity value (Z-axis) at 90-degree cross point is more than a first threshold value; finding a correlation between a motion yaw and a roll between zero-degree and 45-degree; classifying the shoulder motion as abduction, if the correlation between a motion yaw and a roll is greater than a second threshold value classifying the shoulder motion as flexion, if the correlation between the motion yaw and the roll is lesser than a second threshold value; and estimating, via the one or more hardware processors, a range of motion, associated with the shoulder motion classified among one of the extensions, abduction and flexion, using the extracted plurality of feature parameters; and a velocity, an arm movement and a performance score using the extracted plurality of feature parameters.

In yet another aspect, there are provided one or more non-transitory machine-readable information storage mediums comprising one or more instructions which when executed by one or more hardware processors cause capturing a sensor data, specific to a shoulder movement in a plurality of phases, using a smart watch wherein the smart watch is configured to continuously monitor and quantify the shoulder movement; processing, via one or more hardware processors, the transmitted sensor data to extract a plurality of feature parameters specific to the shoulder movement in the plurality of phases; applying, via the one or more hardware processors, a rule-based engine algorithm on the captured sensor data to determine a shoulder motion classification, wherein applying the rule-based engine algorithm comprising: pre-processing a plurality of raw signals in the collected sensor data to obtain a filtered signal using a normalization technique; detecting a plurality of negative peaks using a gradient descent method and a plurality of positive peaks using a modified gradient descent method from the filtered signal; removing a plurality of false positive peaks from the detected plurality of positive peaks and removing a plurality of false negative peaks from the detected plurality of negative peaks using a reverse scanning technique; estimating an instantaneous angle of shoulder (Øs) with respect to thorax or neutral position from the filtered signal; detecting 90-degree cross point using the estimated instantaneous angle of shoulder; finding a corresponding motion gravity value (Z-axis) for the detected 90-degree cross point; classifying the shoulder motion as extension, if the motion gravity value (Z-axis) at 90-degree cross point is more than a first threshold value; finding a correlation between a motion yaw and a roll between zero-degree and 45-degree; classifying the shoulder motion as abduction, if the correlation between a motion yaw and a roll is greater than a second threshold value classifying the shoulder motion as flexion, if the correlation between the motion yaw and the roll is lesser than a second threshold value; and estimating, via the one or more hardware processors, a range of motion, associated with the shoulder motion classified among one of the extensions, abduction and flexion, using the extracted plurality of feature parameters; and a velocity, an arm movement and a performance score using the extracted plurality of feature parameters.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
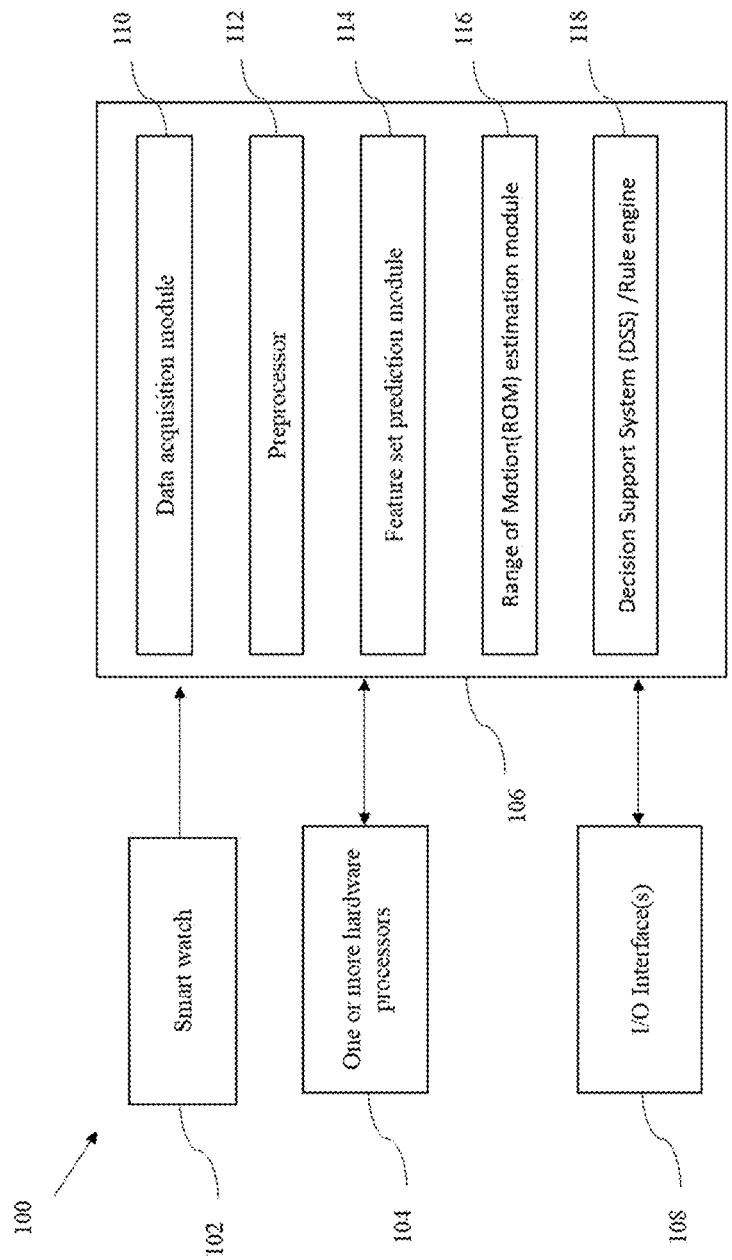
FIG. 1 illustrates an exemplary block diagram of the system for shoulder proprioceptive analysis according to some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

The embodiments herein provide a system 100 and method for shoulder proprioceptive analysis of a person. The present disclosure monitors the shoulder joint motion by quantitative measure of range of motion (ROM) and kinesthesia of shoulder using a smart watch 102, thereby assessing the limit of active motion (without physical movement like jogging or running) and the ability to passively reposition the arm in space. The present disclosure provides objective values to the range of motion in the clinic, therapy and the home environment to speed up and enhance management protocols in both surgical, non-surgical and sports medicine areas. The present disclosure also provides a performance metrics of shoulder function by comparing shoulder motion before and after a prosthesis procedure. Further, the present disclosure predicts the shoulder motion such as flexion, extension, abduction, and adduction, internal and external rotation.

Referring now to the drawings, and more particularly to FIG. 1 through FIG. 8B, where similar reference characters denote corresponding features consistently throughout the figures, there are shown preferred embodiments and these embodiments are described in the context of the following exemplary system and/or method.

FIG. 1 illustrates an exemplary block diagram of the system for shoulder proprioceptive analysis according to some embodiments of the present disclosure. In an embodiment, the system 100 includes a smart watch 102, one or more hardware processors 104, communication interface device(s) or input/output (I/O) interface(s) 108 (also referred as interface(s)), and one or more data storage devices or memory 106 operatively coupled to the one or more hardware processors 104. In an embodiment, the system 100 further includes a data acquisition module 110, a preprocessor 112, a feature set prediction module 114, a Range of Motion (ROM) estimation module 116, a Decision Support System (DSS)/rule engine 118. The one or more processors 104 may be one or more software processing components and/or hardware processors. In an embodiment, the hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) is configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud and the like.

The I/O interface device(s) 108 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 106 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The memory 106 further comprises (or may further comprise) information pertaining to input(s)/output(s) of each step performed by the systems and methods of the present disclosure. In other words, input(s) fed at each step and output(s) generated at each step are comprised in the memory 106 and can be utilized in further processing and analysis.

Figure 4:
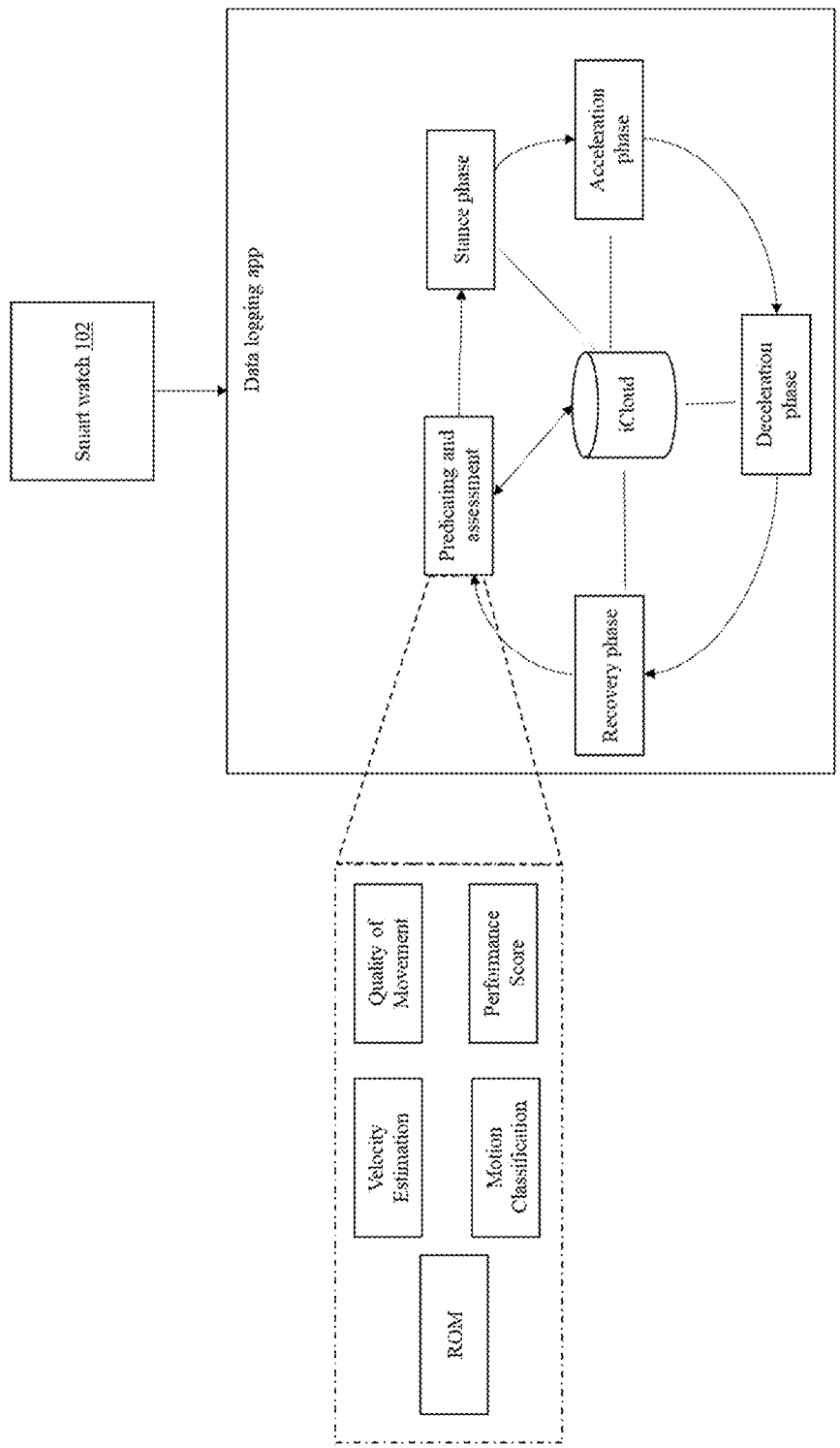
FIG. 4 is a use case illustrating an analytical engine architecture for shoulder proprioceptive analysis in accordance with some embodiments of the present disclosure.

In an embodiment, the system 100 is configured to acquire/capture the sensor data from the smart watch 102 wherein the acquired sensor data would be transmitted to a mobile phone or a laptop or cloud via any wireless communication method such as Wi-Fi, Bluetooth, Near Field Communication (NFC) etc. The smart watch 102 of the system 100 captures the direction of movement, speed and range of motion of the shoulder joint. The Smart watch 102 consists of (inertial measurement unit) IMU sensor, accelerometer, gyroscope and magnetometer which could be a smart watch or band or patch or tattoo. In an example of the present embodiment of the disclosure, the smart watch 102 is used on the right wrist of the participant to maintain the watch orientation across participants, wherein the smart watch 102 is aligned perfectly and facing outside. Further, three principal movements which includes abduction, flexion and extension are studied wherein participants were instructed to repeat each upper limb motion set 3 times. Such repetition of shoulder activities shall not be construed as limiting the scope of the present disclosure. The data acquisition module 110 of the system 100 acquires the sensor data from smart watch 102. The acquired sensor data would be stored in the smart watch 102 and the acquired sensor data will be pushed to a cloud platform either manually by the user or automatically for example, event-based data push or timely data push. Event based data push includes pushing the acquired sensor data during certain repeated shoulder activities wherein, the timely data push includes pushing the acquired sensor data 5 times with regular interval based on a physician recommendation. Such repetition of shoulder activities shall not be construed as limiting the scope of the present disclosure. Further, the acquired sensor data would be preprocessed by the preprocessor module 112 of the system. Further, the feature set prediction module 114 of the system 100 is configured to extract a plurality of feature parameters from the preprocessed sensor data for each phase of shoulder activities, wherein a phase of shoulder may include a stance phase, an acceleration phase, a deceleration phase and a recovery phase as depicted in FIG. 4. Further, the extracted features would be used to detect the range of motion (ROM), velocity, arm movement (flexion, extension and so) and also performance score calculation wherein the present disclosure, rule engine-based approach is used for identifying the shoulder/arm movement and for performance score calculation.

Performance score is calculated by statistical model which includes regression analysis or simply based on physician recommended values. For example $$Pflex_i = \Sigma(TR_{Flex}, V_{Flex}, S_{Flex})$$

$TR_{Flex}$—No of times user able to achieve the targeted/recommended ROM $V_{Flex}$—Velocity during Flexion $S_{Flex}$—Movement smoothness during flexion $$PS = \zeta \sum_{n=1}^{N} (Pflex_i + Pabd_i + Pext_i)$$

Where ζ=1 to 0.5, as day progress the ζ value decreases
The Decision support system (DSS) or rule engine 118 is implemented in the present disclosure to classify the shoulder motion which includes abduction, flexion and extension. The ROM estimation module 116 of the system 100 is configured to estimate the range of motion i.e. the available amount of movement of a joint in different directions which can be either passive, active or active assisted.

Figure 2:
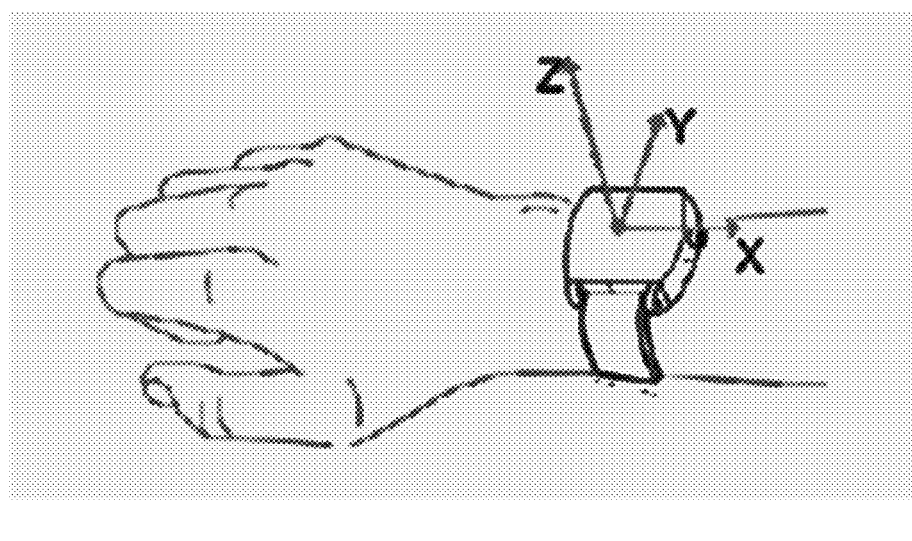
FIG. 2 is a schematic representation of a smartwatch coordination representation for shoulder proprioceptive analysis according to some embodiments of the present disclosure.
Figure 2:

FIG. 2 is a schematic representation of a smartwatch coordination representation for shoulder proprioceptive analysis according to some embodiments of the present disclosure. In the present disclosure the smart which is used on dominant hand or right-hand user coordinate. For example, the smart watch 102 can be used on the right wrist of the user to study/analyses the joint movements of the user. Similarly, smart watch 102 could be re-configured to left wrist as well. In some examples, the coordinates are automatically configured between the right and left hand or dominant and non-dominant hand. For other watch or modality of sensing coordinate configuration has to be selected manually by the user, that has been provided.

Figure 3A:
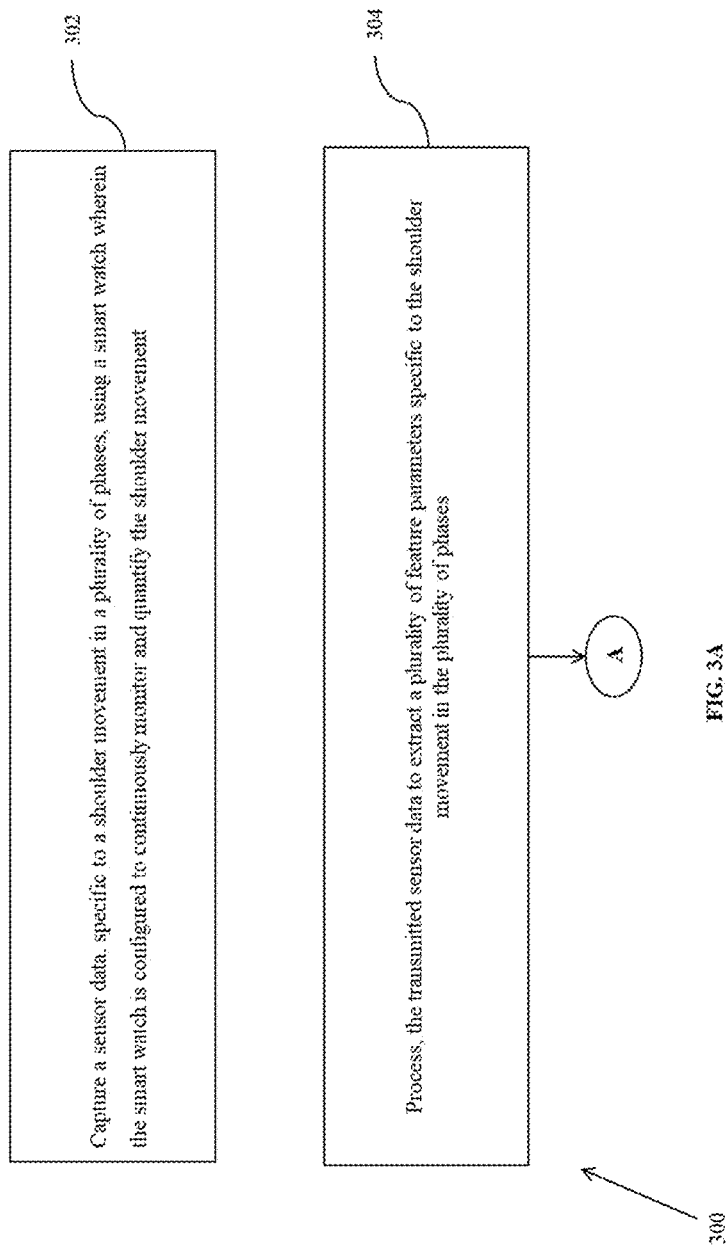
FIGS. 3A and 3B are flowcharts illustrating the steps involved in the method for shoulder proprioceptive analysis, in accordance with some embodiments of the present disclosure.
Figure 3B:
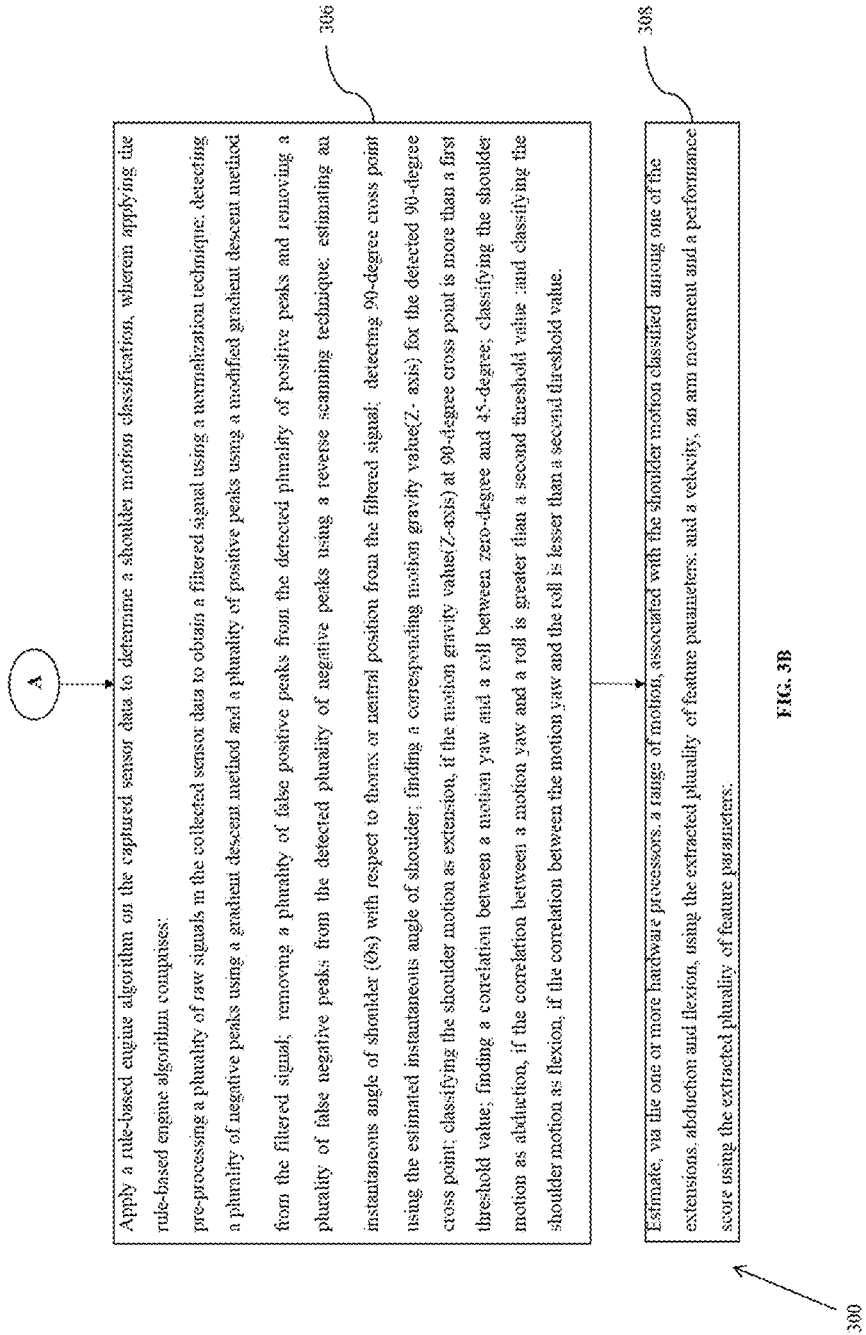

FIGS. 3A and 3B are flowcharts illustrating the steps involved in the method for shoulder proprioceptive analysis, in accordance with some embodiments of the present disclosure. At step 302 of the present disclosure, capturing a sensor data, specific to a shoulder movement in a plurality of phases, using a smart watch 102 wherein the smart watch 102 is configured to continuously monitor and quantify the shoulder movement. At step 304 of the present disclosure, the one or more hardware processors 104 process, the transmitted sensor data to extract a plurality of feature parameters specific to the shoulder movement in the plurality of phases. At step 306 of the present disclosure, apply, via the one or more hardware processors, a rule-based engine algorithm on the captured sensor data to determine a shoulder motion classification, wherein applying the rule-based engine algorithm comprises:
(i) pre-processing a plurality of raw signals in the collected sensor data to obtain a filtered signal using a normalization technique.
(ii) detecting a plurality of negative peaks using a gradient descent method and a plurality of positive peaks using a modified gradient descent method from the filtered signal.
(iii) removing a plurality of false positive peaks from the detected plurality of positive peaks and removing a plurality of false negative peaks from the detected plurality of negative peaks using a reverse scanning technique.
(iv) estimating an instantaneous angle of shoulder (Øs) with respect to thorax or neutral position from the filtered signal.
(v) detecting 90-degree cross point using the estimated instantaneous angle of shoulder.
(vi) finding a corresponding motion gravity value (Z-axis) for the detected 90-degree cross point.
(vii) classifying the shoulder motion as extension, if the motion gravity value (Z-axis) at 90-degree cross point is more than a first threshold value, i.e., for example, $\sin^{-1}(-0.5)$. Such values shall not be construed as limiting the scope of the present disclosure.
(viii) finding a correlation between a motion yaw and a roll between zero-degree and 45-degree.
(ix) classifying the shoulder motion as abduction, if the correlation between a motion yaw and a roll is greater than a second threshold value i.e. (Correlation (motion yaw (45° and roll (MINVALUE)>−0.5 & Correlation (motion yaw and roll(MAXVALUE)<−0.4)

if corr(YR)>*th*2 then Abduction else Flexion and
(x) classifying the shoulder motion as flexion, if the correlation between the motion yaw and the roll is lesser than a second threshold value.

At 308 of the present disclosure, estimate, via the one or more hardware processors,
(a) a range of motion, associated with the shoulder motion classified among one of the extensions, abduction and flexion, using the extracted plurality of feature parameters; and
(b) a velocity, an arm movement and a performance score using the extracted plurality of feature parameters;

FIG. 4 is a use case illustrating an analytical engine architecture for shoulder proprioceptive analysis in accordance with some embodiments of the present disclosure. In an example of the present embodiment of the disclosure, for development and validation purpose, a study protocol is considered wherein the data related to shoulder activities is collected in two-phase namely a first phase and a second phase. The first phase includes controlled or stepwise motion of hand for range of motion (ROM) and velocity estimation and validation, and second phase includes natural movement of hand for shoulder motion identification and validation. However, in real-time, only second phase is considered wherein the ROM for shoulder motion is identified and estimated. In this study protocol, for first phase, 25 healthy participants with a mean age of 28±4, height of 161.1±1.96 cm and body mass of 60.1±7.13 kg and in second phase, 50 healthy participants with age of 30±3; with 25% of first phase, participants overlap. The three principal movements were tested in this study which includes abduction, flexion and extension. However, the same can be extended to internal and external rotation, and circumduction action as well. For this study, the inclusion criteria was any healthy adult from 20-50 years of age, who had no history of upper limb injury or disease, no history of movement disorders, no history of shoulder disease or treatment for shoulder pain and no known neurological disorders, either central or peripheral that had the potential to impair their participation in the study. The smart watch 102 was used on the right wrist of the participant and to maintain the smart watch 102 orientation across participants, the smart watch 102 was kept aligned perfectly and facing outside.

Referring to FIG. 4, the data collection for different phase of hand movement such as stance phase, acceleration phase, deceleration phase and recovery phase is illustrated. The first phase data collection protocol includes participant standing in a neutral position wherein this position of rest is with the upper limb by the side of the body with palm touching the thigh. The data recording was started by an investigator with an initial 10 sec of waiting time in the neutral position. The participant was instructed to start the upper limb motion, for example Flexion. This is detailed as follows:

Acceleration Phase

Lift the right hand in forward direction, to an angle of 45°. (Palm facing the ground).

The waiting period for manual measurement using goniometer

Move forward toward an approximate angle of 90°.

The waiting period for manual measurement using goniometer

Move the right hand to an angle of 135°.

The waiting period for manual measurement using goniometer

Move the right hand to an angle of 180°/max degrees. (Thumb pointing to the left)

The waiting period for manual measurement is done.

Referring to FIG. 4, during deceleration phase vice versa of acceleration phase would be performed (i.e. 180°-135°-90°-45°) with manual measurement and investigator shall stop the recording. Similarly, data collection process would be adapted for abduction activities as well. In case of extension, participants were instructed to move the hand for extension (i.e. backward direction) to a maximum distance without changing their posture wherein during the wait time at once the max (instantaneous) angle is noted manually during the waiting/hold position, participants would move to a neutral position and wait for 5 sec. Later, the investigator shall stop recording in the smart watch 102. Further, in the second phase data collection protocol, the participants were instructed to perform flexion, extension, and abduction without resting or waiting period. The investigator shall start and stop the recording in the smart watch 102. However, in real time the above-mentioned process is automatic, or the user can start and stop the recording in smartwatch 102 and tattoo or modality respectively.

Referring to FIG. 2 and FIG. 4, sensor position during data establishment is characterized by its location (left or right hand), placement (smart watch 102 crown directed toward the palm or elbow) and orientation. Further, in order to maintain the homogeneity of the study, the dominant wrist movements which includes dominant hand or right-hand user coordinate are investigated, as depicted in FIG. 2. Raw dataset collected form the smart watch 102 composed of time series of IMU sensor or integrated unit of accelerometer, gyroscope and magnetometer data wherein the watch is worn to a user's hand and used to record the hand movement data using a 3rd party sensor logging app or stand-alone app developed on smart watch 102, specific app. Further the data were sampled from the smart watch 102 at a frequency as suggest by Shannon sampling rate; for example, 30 Hz, wherein each sample in the data set was composed of the in-built sensor of the smart watch 102 for one complete action which includes stance phase (no action), acceleration phase of the hand, deceleration phase and recovery phase or neutral position. Once the data is recorded by the logging app, it would be pushed to cloud for off-line analysis as depicted in FIG. 4. In an embodiment, smart watch 102 data could be streamed directly to phone or laptop depending on the specification and configuration of the smart watch 102. For example, the proposed smart watch 102 allow to stream the data to the mobile phone. Further, as a validation process, to test the ROM algorithm, the smart watch 102, was attached to the movable arm of the goniometer and the recording of angle for every 45 degree for validate the ROM and velocity. The dataset comprised in the goniometer is called as Gonio-data. Later, the participants wear the watch and recording of the hand movement was done for 3 specified motions of flexion, extension, and abduction. To assess the accuracy of the algorithm between the goniometer and the smart watch 102 in a participant, only active ROM was tested. On the other hand, for the motion classification algorithm validation, approximately maximal ROM (angles) of a participant were recorded during flexion and abduction, and extension correspondingly. Further, to detect the various shoulder motion or to classify the shoulder motion, a rule engine based (REb) algorithm is developed as depicted in FIG. 4, which also estimates the performance score and various movement of arm of each phase of action or motion or activities as depicted in FIG. 4.

Figure 5:
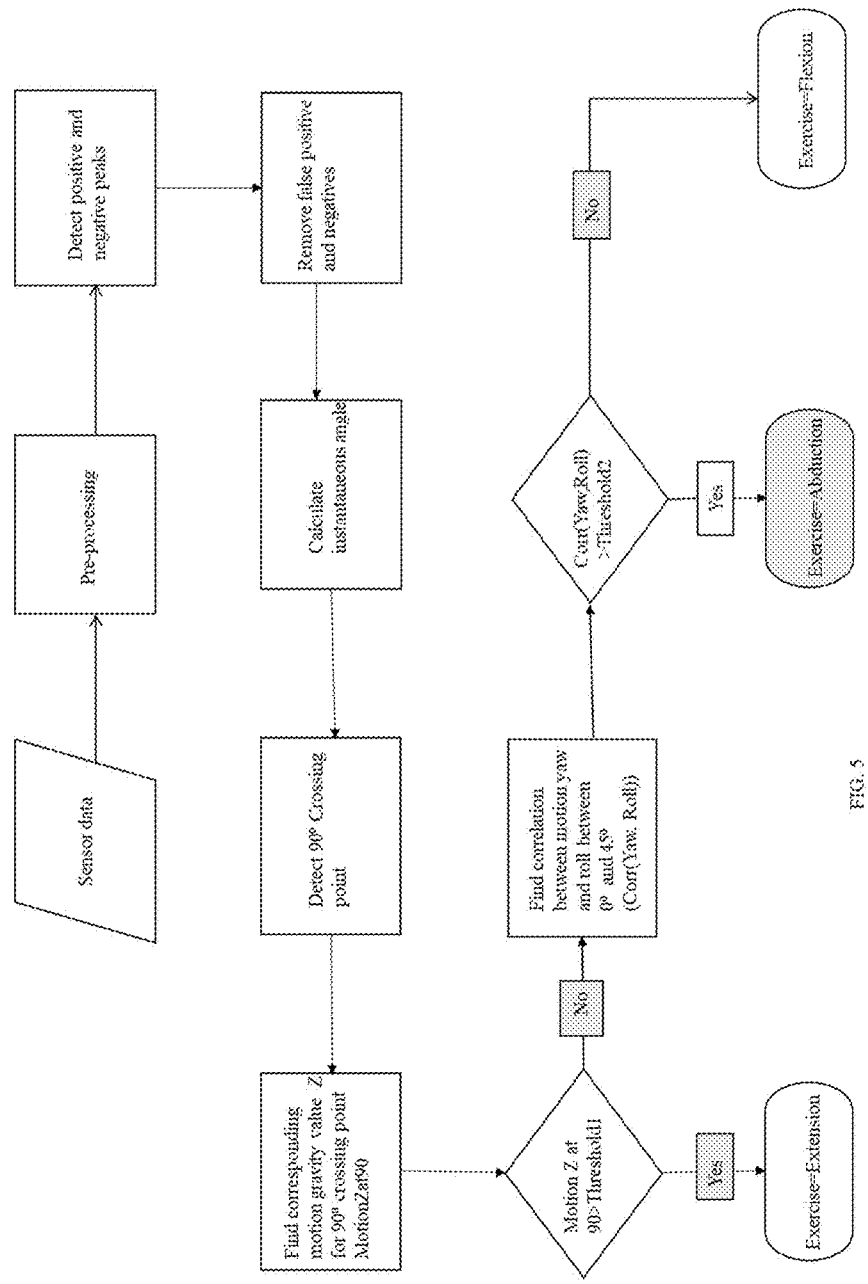
FIG. 5 is a flow chart illustrating the rule-based engine algorithm for motion classification during shoulder proprioceptive analysis according to some embodiments of the present disclosure.

FIG. 5 is a flow chart illustrating the rule-based engine algorithm for motion classification during shoulder proprioceptive analysis according to some embodiments of the present disclosure. Referring to FIG. 5, the sensor data (xs), collected from smart watch 102, is pre-processed using any normalized approach, for example, 3rd order Butterworth filter to obtain a plurality of filtered signals. Further, the plurality of filtered signals (xf) was processed to detect the positive and negative peaks and a reverse scanning was performed to remove the false positive and negative peaks wherein the false peak was discarded and the instantaneous angle of shoulder (Øs) with respect to ground is estimated. This approach of estimating angle of shoulder was applied to the Motion gravity Z (Øsz) and its maximum instantaneous angle or 90°, whichever is greater, is estimated and were compared with a threshold value (th1) as depicted by the equation 1.

If Øsz>th1 then Extension

Else No action     (1)

If 'No' has been detected, then the correlation between motion-yaw and motion-roll corresponding to instantaneous angles in the range of 0° to 45° as depicted by the equation 2.

If corr(YR)>th1 then Abduction

Else Flexion     (2)

In an embodiment, as a part of the statistical analysis, each trial from the smart watch sensor data 102 was processed, and a shoulder angle was estimated from the smart watch 102 sensor data. Further, the estimated shoulder angle is compared which is further compared with manual goniometer to determine the accuracy of the REb algorithm using root mean square error ($RMS_{error}$)

$$(RMS_{error}) = \sqrt{\sum_{i=0}^{n} (x_{o_k} - x_{e_k})^2 / N}$$

which represent the mean error between the ground truth $x_{o_k}$ (goniometer) and estimated (smart watch 102 data) $x_{e_k}$, and N represents the total number of iterations for a step of 45 degrees. Bland-Altman plots were also performed for specified range of motion (ROM) such as 45°, 90°, 135°, and 180°; to understand the difference between the measurements of the estimated ROM ($x_{e_k}$) from watch and goniometer ($x_o$). Further for the range of motion (ROM) estimation, 25 health participants participated, wherein each performed 3 tasks (flexion, extension, abduction) with a repetition of 3 times for each position (45, 90, 135, 180 degrees) of shoulder motion.

TABLE 1

RANGE OF MOTION ACCURACY ESTIMATION USING SMARTWATCH

| Movements | No. of trial | Degrees | Error in degrees | $RMS_{error}$ |
|---|---|---|---|---|
| Flexion | 70 | 45° | 6.8 | 9.3 |
|  | 70 | 90° | 8.5° | 11 |
|  | 70 | 135° | 9.9° | 13.55 |
|  | 70 | 180° | 9.9° | 12.51 |

TABLE 1-continued

RANGE OF MOTION ACCURACY ESTIMATION
USING SMARTWATCH

| Movements | No. of trial | Degrees | Error in degrees | $RMS_{error}$ |
|---|---|---|---|---|
| Abduction | 65 | 45° | 5.8° | 9.55 |
|  | 65 | 90° | 8.85° | 12.01 |
|  | 65 | 135° | 12.1° | 14.19 |
|  | 65 | 180° | 10.1° | 14.33 |
| Extension | ~64 | Max | 10 | 12.07 |
|  | Average |  | 9.1 | 12.05 |

Table 1 shows the $RMS_{error}$ between the estimated ROM ($x_{e_k}$) and goniometer measure wherein the result infers the error of 9°.

Figure 6:
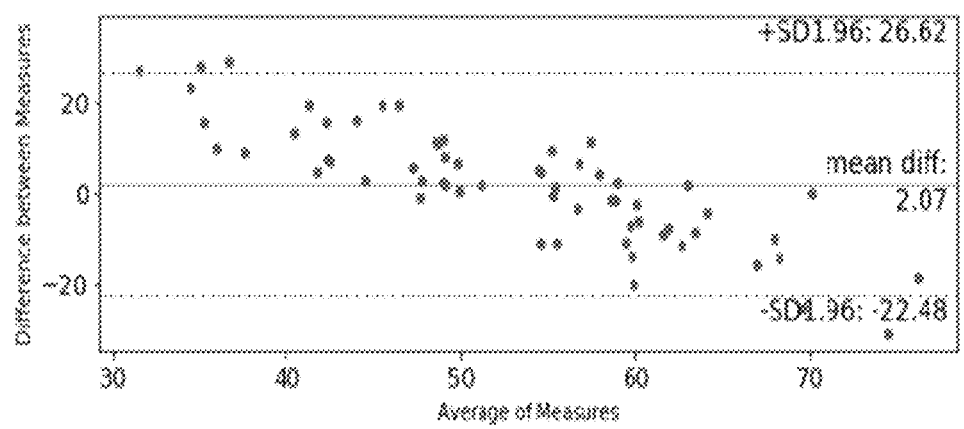
FIG. 6 is a use case illustrating an extension Bland-Altman plots of difference between the average of angles measured using goniometer against the smartwatch for shoulder proprioceptive analysis in accordance with some embodiments of the present disclosure.

FIG. 6 is a use case illustrating an extension Bland-Altman plots of difference between the average of angles measured using goniometer against the smartwatch for shoulder proprioceptive analysis in accordance with some embodiments of the present disclosure. Referring to FIG. 6, the Bland-Altman plots in agreement with the MSRerror result, which shows discrepancies between the estimated ROM (xek) and goniometer measures reported a mean difference of 2.07±1.96 between the 'true' goniometer and ROMest for extension shoulder function. Thus, Bland-Altman plots show that <2% of the estimated angle measured was out of the boundary of goniometry measurement for extension.

Figure 7A:
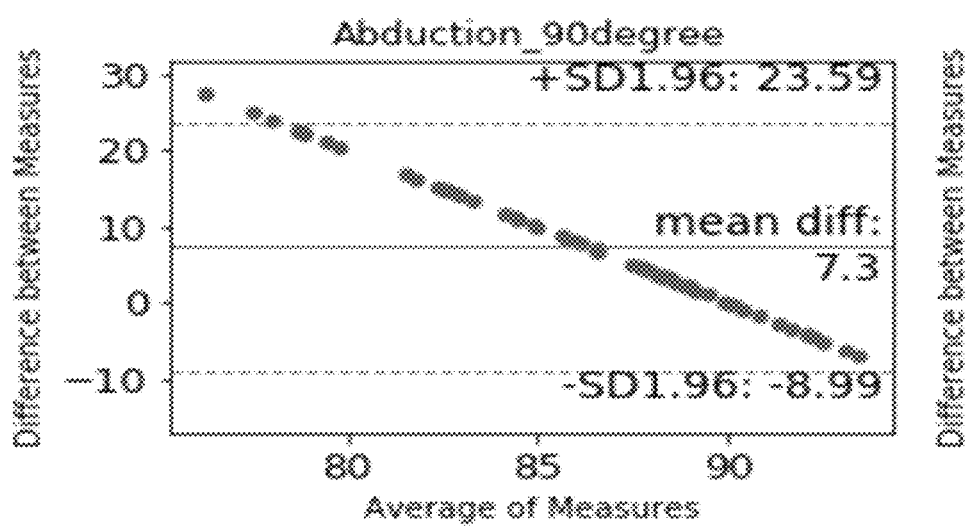
FIGS. 7A and 7B are use cases illustrating an abduction Bland-Altman plots of difference between the average of angles measured using goniometer against smart watch for shoulder proprioceptive analysis, in accordance with some embodiments of the present disclosure.
Figure 7B:
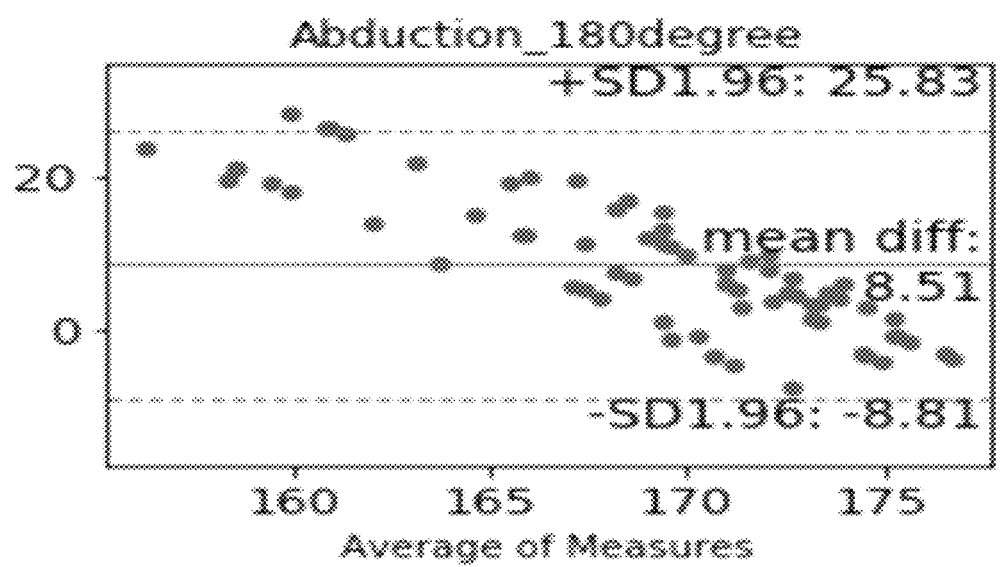

FIGS. 7A and 7B are use cases illustrating an abduction Bland-Altman plots of difference between the average of angles measured using goniometer against smart watch for shoulder proprioceptive analysis, in accordance with some embodiments of the present disclosure. Referring to FIGS. 7A and 7B, the Abduction Bland-Altman plots in agreement with the MSRerror result, which shows discrepancies between the estimated ROM (xek) and goniometer measures reported a mean difference of 7.3±1.96 and 8.51±1.96 between the 'true' goniometer and ROMest for shoulder Abduction function at 90° and 180° respectively.

Figure 8A:
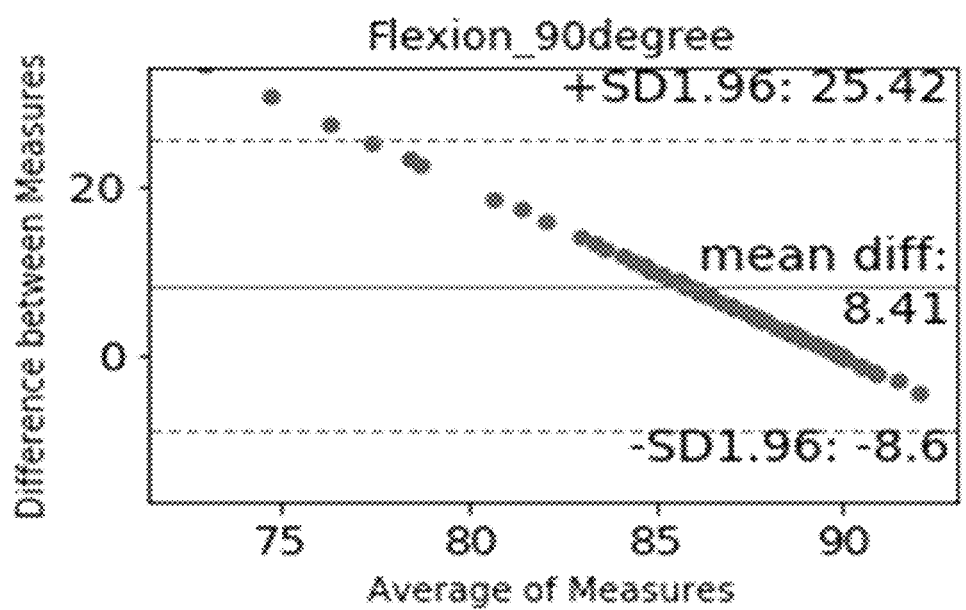
FIGS. 8A and 8B are use cases illustrating a flexion Bland-Altman plots of difference between the average of angles measured using goniometer against smart watch for shoulder proprioceptive analysis, in accordance with some embodiments of the present disclosure.
Figure 8B:
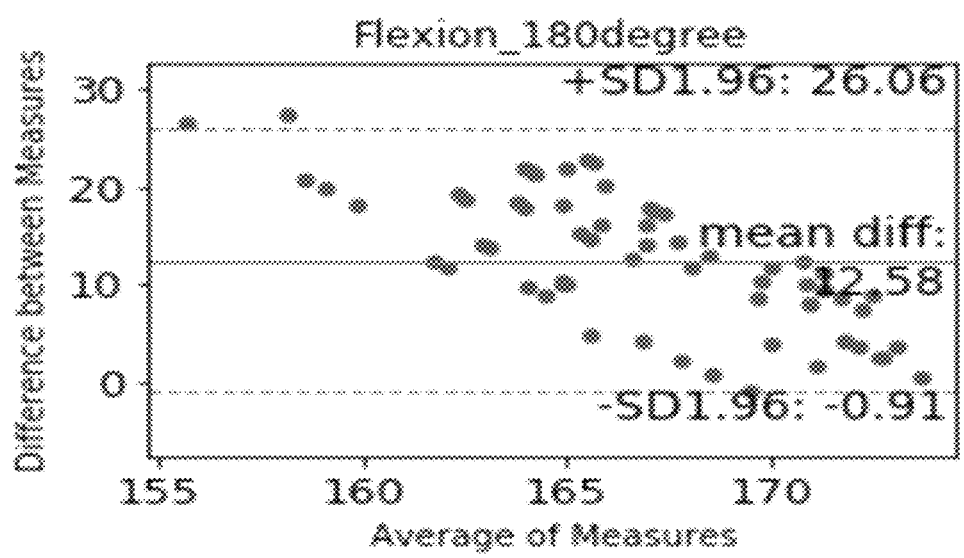

FIGS. 8A and 8B are use cases illustrating a flexion Bland-Altman plots of difference between the average of angles measured using goniometer against smart watch for shoulder proprioceptive analysis, in accordance with some embodiments of the present disclosure. Referring to FIGS. 8A and 8B, the Flexion of 90° and 180° shows discrepancies between the estimated ROM (xek) and goniometer measures reported a mean difference of 8.41±1.96 and 12.58±1.96 respectively compared to 7.3±1.96 and 8.51±1.96 for shoulder abduction wherein the results infer that the present method achieved smaller deviations around bias with now outliers for achieved smaller deviations around bias with now outliers for all the indices over 95% confidence interval. Thus, suggest that the range of motion (ROM) estimated (xek) metric could be a surrogate of reported traditional shoulder ROM metrics.

In an embodiment, the raw data collected for range of motion (ROM) estimation was used for shoulder motion identification. Even though range of motion (ROM) validation was performed for the targeted degrees, for motion identification full cycle of data was considered i.e. starting to end of one motion, say flexion and it has been observed that clear distinguishable pattern pertains between flexion and extension as shown in table 2 which leads to 100% accuracy of extension classification or identification.

TABLE 2

Performance comparison matrix for various shoulder motion
(Flex—Flexion; ABD—Abduction; Ext—Extension)
using Rule engine-based algorithm.

|  | Flex | Abd | Ext | Class Overview | Precision |
|---|---|---|---|---|---|
| Flex | 90 | 0 | 0 | 90 | 100% |
| Abd | 19 | 72 | 0 | 91 | 79.12% |
| Ext | 3 | 0 | 89 | 92 | 96.74% |
| Truth Overall | 112 | 72 | 89 | 273 |  |
| Recall | 80.35% | 100% | 100% |  |  |

Hence, the present disclosure provides a system and method for shoulder proprioceptive analysis of the person. The present disclosure aims to assess the proprioception of shoulders functional movement, while a shoulder motion is performed in 3 planes of humerothoracic elevation wherein by comparing the differences in glenohumeral joint angular motion and linear translations between before and after an event, for example, the event could be a surgery or injury. Further, this shoulder movement could be evaluated under various condition such as passive, active and against restricted movement wherein shoulder movement could be assessed further either in a controlled or daily routine day environment with a close or open kinetic mode of operation. Particularly, the proprioception of shoulders range of motion (ROM) and velocity are the biomarker to evaluate the performance of an individual. Further, the shoulder movements also have components of scapular motion which adds to true glenohumeral movements to provide the enhanced and combined range of motion of the shoulder wherein these methods would be subject to inherent inter-observer variation and intra observer variation as well as error in the actual quantification of motion parameters. The present disclosure is advantageous to know to what extent there is true glenohumeral mobility and how much the patient is compensating with other movements in the real-life scenarios. Also, the present disclosure is advantageous with the rapid rise in indications for shoulder reconstruction, to know what actual benefits have accrued by accurate monitoring of range of motion and quantification of the same. In this present disclosure shoulder proprioception performance index/score is estimated by monitoring the before, and after surgical stabilization of an individual shoulders data collected using external SPA brace/sensors and assessing threshold to detection of passive motion and the ability to passively reposition the arm in space. Further, kinaesthesia is defined as the sensation of the motion to locate the different parts of the body and to evaluate their movement (velocity and direction) and the static part is named statesthesia is estimated using the smart watch data. The built-in inertial sensors allow detecting and monitoring both linear and angular movements of the shoulder or other joints where in the system could also be integrated with interactive systems such as a display, an audio alert, or a tactile feedback system. Further, proprioceptive performance index resulting either from diseases, accidents, trauma, surgery, or normal ageing may lead to necessitating specific rehabilitation to prevent injuries and reduce balance deficits.

According to an embodiment of the present disclosure, the system and method for shoulder proprioceptive analysis of the person includes the following applications:

Continuous shoulder monitoring, remote monitoring for ROM to facilitate recovery from shoulder related ailments wherein ROM is an important criterion for shoulder functional recovery.

Shoulder Function analysis of an individual during ADL (Activities of Daily Living) wherein the exact amount of motion of the shoulder in various activities of daily living estimated is valuable information to clinicians, researchers and therapists.

Objective record of recovery from injury/surgery/painful condition i.e. a linear trending of ROM recordings between visits is extremely valuable in understanding the process of recovery and tailoring appropriate interventions.

Causal insights leveraging post-operative outcomes using actionable in-sights mining Mode of Operation
  Manual intervention
  Manual Approach: GUI
Automatic intervention
Distinguish between left and right upper limb
Smart watch configuration
Shoulder movement quantification
Hand tremor identification
Shoulder proprioception index (Pre & Post surgery)
Shoulder motion evaluation in sports wherein, sports is an important area in professional athletics which will help in fine tuning the recovery process in the case of athletes recovering from sports related injuries and overuse patterns.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor-implemented method, comprising:
  capturing a sensor data, specific to a shoulder movement in a plurality of phases, using a smart watch wherein the smart watch is configured to continuously monitor and quantify the shoulder movement (302);
  processing, via one or more hardware processors, the captured sensor data to extract a plurality of feature parameters specific to the shoulder movement in the plurality of phases (304), wherein the feature parameters comprising motion gravity 'Y', motion gravity 'Z', a motion roll and a motion yaw;
  applying, via the one or more hardware processors, a rule-based engine algorithm on the captured sensor data to determine a shoulder motion classification, wherein applying the rule-based engine algorithm comprising (306):
    pre-processing a plurality of raw signals in the captured sensor data to obtain a filtered signal using a normalization technique;

detecting a plurality of negative peaks using a gradient descent method and a plurality of positive peaks using a modified gradient descent method from the filtered signal;

removing a plurality of false positive peaks from the detected plurality of positive peaks and removing a plurality of false negative peaks from the detected plurality of negative peaks using a reverse scanning technique;

estimating an instantaneous angle of shoulder (Os) with respect to thorax or neutral position from the filtered signal;

detecting 90-degree cross point using the estimated instantaneous angle of shoulder;

finding the corresponding motion gravity value (Z-axis) for the detected 90-degree cross point;

classifying the shoulder motion as extension, if the motion gravity value (Z-axis) at 90-degree cross point is more than a first threshold value;

finding a correlation between the motion yaw and the motion roll between zero-degree and 45-degree;

classifying the shoulder motion as abduction, if the correlation between the motion yaw and the motion roll is greater than a second threshold value and;

classifying the shoulder motion as flexion, if the correlation between the motion yaw and the motion roll is lesser than the second threshold value;

estimating, via the one or more hardware processors, (i) a range of motion, associated with the shoulder motion classified among one of the extensions, abduction and flexion, using the extracted plurality of feature parameters, wherein the range of motion estimated based on the available amount of movement of a joint in different directions in one of passive, active or active assisted, wherein the step of estimating the range of motion includes estimating the range of motion during at least one of maximal shoulder activity, relative shoulder activity, and pre and post an event; and (ii) a velocity, an arm movement and a performance score using the extracted plurality of feature parameters (308), wherein proprioception of shoulders functional movement is assessed while a shoulder motion is performed in 3 planes of humerothoracic elevation by comparing the differences in glenohumeral joint angular motion and linear translations between before and after the event.

2. The method of claim 1, wherein the sensor data is captured using a time series IMU sensor (accelerometer, a gyroscope and a magnetometer) present on the smart watch and the sensor data and the sensor data is transmitted to at least one of a mobile phone, a laptop or a cloud server, via a wireless communication method for processing.

3. The method of claim 1, wherein the plurality of phases comprises a stance phase of hand, an acceleration phase of hand, a deceleration phase of hand and a recovery phase of hand.

4. The method of claim 1, wherein the sensor data comprises one or more of a mean, a median, a slope of the data and a time domain features.

5. The method of claim 1, wherein determining the accuracy of the rule engine-based algorithm further comprises comparing the estimated instantaneous angle of shoulder (Os) with a manual goniometer using a root mean square error.

6. The method of claim 1, wherein the step of estimating the velocity of the shoulder movement includes quantification of the performance score, analyzing a trend and adherence to a rehab.

7. The processor implemented method of claim 1, further comprising remotely monitoring the shoulder movement using the estimated range of motion.

8. The processor implemented method of claim 1, wherein the event comprises a medical operation, an injury or a surgery.

9. A system (100), comprising:
a memory (106) storing instructions;
one or more communication interfaces (108); a smart watch (102); and
one or more hardware processors (104) coupled to the memory (106) via the one or more communication interfaces (108), wherein the one or more hardware processors (104) are configured by the instructions to:
capture a sensor data, specific to a shoulder movement in a plurality of phases, using a smart watch wherein the smart watch is configured to continuously monitor and quantify the shoulder movement;

process, via the one or more hardware processors, the transmitted captured sensor data to extract a plurality of feature parameters specific to the shoulder movement in the plurality of phases, wherein the feature parameters comprising motion gravity 'Y', motion gravity 'Z', a motion roll and a motion yaw;

apply, via the one or more hardware processors, a rule-based engine algorithm on the captured sensor data to determine a shoulder motion classification, wherein applying the rule-based engine algorithm comprises:

pre-processing a plurality of raw signals in the collected captured sensor data to obtain a filtered signal using a normalized technique;

detecting a plurality of negative peaks using a gradient descent method and a plurality of positive peaks using a modified gradient descent method from the filtered signal;

removing a plurality of false positive peaks from the detected plurality of positive peaks and removing a plurality of false negative peaks from the detected plurality of negative peaks using a reverse scanning technique;

estimating an instantaneous angle of shoulder (Os) with respect to ground from the filtered signal;

detecting 90-degree cross point using the estimated instantaneous angle of shoulder;

finding the corresponding motion gravity value (Z) for the detected 90-degree cross point;

classifying the shoulder motion as extension, if the motion gravity value (Z) at 90-degree cross point is more than a first threshold value;

finding a correlation between the motion yaw and the motion roll between zero-degree and 45-degree;

classifying the shoulder motion as abduction, if the correlation between the motion yaw and the motion roll is greater than a second threshold value and;

classifying the shoulder motion as flexion, if the correlation between the motion yaw and the motion roll is lesser than the second threshold value;

estimating, via the one or more hardware processors,
(i) a range of motion, associated with the shoulder motion classified among one of the extensions, abduction and flexion, using the extracted plurality of feature parameters, wherein the range of motion estimated based on the available amount of movement of a joint in different directions in one of passive, active or active assisted, wherein the step of estimating the range of motion includes estimating the range of motion during at least one of maximal shoulder activity, relative shoulder activity, and pre and post an event; and (ii) a velocity, an arm movement and a performance score using the extracted plurality of feature parameters (308), wherein proprioception of shoulders functional movement is assessed while a shoulder motion is performed in 3 planes of humerothoracic elevation by comparing the differences in glenohumeral joint angular motion and linear translations between before and after the event.

10. The system as claimed in claim 9, wherein the sensor data is captured using a time series IMU sensor (accelerometer, a gyroscope and a magnetometer) present on the smart watch and the sensor data is transmitted to at least one of a mobile phone, a laptop or a cloud server, via a wireless communication method for processing.

11. The system as claimed in claim 9, wherein the plurality of phases comprises a stance phase of hand, an acceleration phase of hand, a deceleration phase of hand and a recovery phase of hand.

12. The system as claimed in claim 9, wherein the sensor data comprises one or more of a mean, a median, a slope of the data and a time domain features.

13. The system as claimed in claim 9, wherein determining the accuracy of the rule engine-based algorithm further comprises comparing the estimated instantaneous angle of shoulder ($\emptyset s$) with a manual goniometer using a root mean square error.

14. The system as claimed in claim 9, wherein the step of estimating the velocity of the shoulder movement includes quantification of the performance score, analyzing a trend and adherence to a rehab.

15. The system as claimed in claim 9, further comprising remotely monitoring the shoulder movement using the estimated range of motion.

16. The system as claimed in claim 9, wherein the event comprises a medical operation, an injury or a surgery.

17. One or more non-transitory machine readable information storage mediums comprising one or more instructions which when executed by one or more hardware processors cause:
capturing a sensor data, specific to a shoulder movement in a plurality of phases, using a smart watch wherein the smart watch is configured to continuously monitor and quantify the shoulder movement;
processing, via one or more hardware processors, the captured sensor data to extract a plurality of feature parameters specific to the shoulder movement in the plurality of phases;
applying, via the one or more hardware processors, a rule-based engine algorithm on the captured sensor data to determine a shoulder motion classification, wherein applying the rule-based engine algorithm comprising:
pre-processing a plurality of raw signals in the collected captured sensor data to obtain a filtered signal using a normalization technique;
detecting a plurality of negative peaks using a gradient descent method and a plurality of positive peaks using a modified gradient descent method from the filtered signal;
removing a plurality of false positive peaks from the detected plurality of positive peaks and removing a plurality of false negative peaks from the detected plurality of negative peaks using a reverse scanning technique;
estimating an instantaneous angle of shoulder ($\emptyset s$) with respect to thorax or neutral position from the filtered signal;
detecting 90-degree cross point using the estimated instantaneous angle of shoulder;
finding the corresponding motion gravity value (Z-axis) for the detected 90-degree cross point;
classifying the shoulder motion as extension, if the motion gravity value (Z-axis) at 90-degree cross point is more than a first threshold value;
finding a correlation between the motion yaw and the motion roll between zero-degree and 45-degree;
classifying the shoulder motion as abduction, if the correlation between the motion yaw and the motion roll is greater than a second threshold value and;
classifying the shoulder motion as flexion, if the correlation between the motion yaw and the motion roll is lesser than the second threshold value;
estimating, via the one or more hardware processors,
(i) a range of motion, associated with the shoulder motion classified among one of the extensions, abduction and flexion, using the extracted plurality of feature parameters, wherein the range of motion estimated based on the available amount of movement of a joint in different directions in one of passive, active or active assisted, wherein the step of estimating the range of motion includes estimating the range of motion during at least one of maximal shoulder activity, relative shoulder activity, and pre and post an event; and
(ii) a velocity, an arm movement and a performance score using the extracted plurality of feature parameters (308), wherein proprioception of shoulders functional movement is assessed while a shoulder motion is performed in 3 planes of humerothoracic elevation by comparing the differences in glenohumeral joint angular motion and linear translations between before and after the event.

18. The non-transitory machine readable information storage mediums of claim 17, wherein the event comprises a medical operation, an injury or a surgery.

* * * * *